US00PP18695P2

(12) United States Plant Patent
Utecht

(10) Patent No.: US PP18,695 P2
(45) Date of Patent: Apr. 1, 2008

(54) ***PELARGONIUM* PLANT NAMED 'GRADORED'**

(50) Latin Name: *Pelargonium×hortorum*
Varietal Denomination: Gradored

(75) Inventor: Angelika Utecht, Montabaur (DE)

(73) Assignee: Florfis AG, Binningen (CH)

( * ) Notice: Subject to any disclaimer, the term of this patent is extended or adjusted under 35 U.S.C. 154(b) by 0 days.

(21) Appl. No.: 11/505,731

(22) Filed: Aug. 17, 2006

(51) Int. Cl.
*A01H 5/00* (2006.01)

(52) U.S. Cl. ..... Plt./330

(58) Field of Classification Search ..... Plt./330
See application file for complete search history.

(56) References Cited

PUBLICATIONS

UPOV–ROM GTITM, Plant Variety Database, 2007/01, GTI Jouve Retrieval Software, Citation for *Pelargonium* 'Gradored' and 'Fiv 279', 2 pages.*

Flora–Nova Pflanzen GmbH [online] [retrieved on Jul. 30, 2007]. Retrieved from the Internet: <http://www.top500.de/details/475/flora–nova_pflanzen_gmbh_germany.php> 2 pages.*

* cited by examiner

*Primary Examiner*—Kent Bell
*Assistant Examiner*—June Hwu
(74) *Attorney, Agent, or Firm*—Jondle & Associates, P.C.

(57) ABSTRACT

A new cultivar of *pelargonium* particularly characterized by having red to orange-red, double and stellar-type flowers, small to medium-sized, tight and semi-spherically shaped umbels on long peduncles, medium-green, fan-shaped foliage with distinct zonation, a vigorous growth habit, a medium to tall, rounded, well-branched, moderately tight plant habit, and a mid-season flowering response, is disclosed.

1 Drawing Sheet

Genus and species: *Pelargonium×hortorum.*
Variety denomination: 'Gradored'.

BACKGROUND OF THE NEW PLANT

The present invention comprises a new and distinct cultivar of *pelargonium,* botanically known as *Pelargonium× hortorum,* and hereinafter referred to by the cultivar name 'Gradored'. The new cultivar is a product of a planned breeding program which had the objective of creating new varieties in various flower colors having stellar-type flowers, medium-green foliage with zonation. 'Gradored' was discovered as a seedling resulting from the cross of the female parent 'K99-4006-2' (unpatented), a proprietary *pelargonium* plant having light-salmon, single-type flowers and the male parent 'K00-5693-7' (unpatented) a proprietary *pelargonium* plant having rose-red, double flowers.

The new cultivar was created in 2001 in Hillscheid, Germany and has been asexually reproduced repeatedly by vegetative cuttings in Galdar, Gran Canaria, Spain, and Hillscheid, Germany over a four-year period. 'Gradored' has been found to retain its distinctive characteristics through successive asexual propagations. 'Gradored' reproduces true to type in successive generations of asexual reproduction.

Plant Breeder's Rights for this cultivar were applied for in Germany on Apr. 4, 2005 and Canada on Apr. 20, 2005.

SUMMARY OF THE INVENTION

The following are the most outstanding and distinguishing characteristics of this new cultivar when grown under normal horticultural practices in Hillscheid, Germany.

1. Red to orange-red, double and stellar-type flowers;
2. Small to medium-sized, tight and semi-spherically shaped umbels on long peduncles;

3. Medium-green, fan-shaped foliage with distinct zonation;
4. A medium to tall plant habit with vigorous growth;
5. A rounded, well-branched and moderately tight plant habit; and
6. A mid-season flowering response.

DESCRIPTION OF THE PHOTOGRAPH

This new *pelargonium* plant is illustrated by the accompanying photograph which shows overall plant habit including inflorescences, buds, and foliage of the plant; the colors shown are as true as can be reasonably obtained by conventional photographic procedures. The photograph, taken in June 2004, is of a 15-week-old, un-pinched plant grown from rooted cuttings in 14-cm pots and grown under greenhouse and outdoor conditions which approximate those generally used in commercial practice.

DESCRIPTION OF THE NEW CULTIVAR

The following detailed description sets forth the distinctive characteristics of 'Gradored'. The data which define these characteristics were collected from asexual reproductions carried out in Hillscheid, Germany. The plant history was taken on 12-week old, un-pinched plants in 12-cm pots in a greenhouse during late May. Color readings were taken under natural light in late May from flowers grown in the greenhouse. Color references are primarily to the RHS Colour Chart of The Royal Horticultural Society of London (RHS) (2001).

DETAILED BOTANICAL DESCRIPTION

Classification:

*Family.*—Geraniaceae.

*Botanical.*—*Pelargonium×hortorum.*

*Common name.*—Zonal geranium, stellar type.

Parentage:

*Female parent.*—'K99-4006-2' a proprietary *pelargonium* plant having light-salmon, single-type flowers (unpatented).

*Male parent.*—'K00-5693-7', a proprietary *pelargonium* plant having rose-red, double flowers (unpatented).

Plant:

*Form.*—Shrub, self-branching, mounding.

*Branching habit.*—9 to 12 branches per plant.

*Height* (*measured from base of the stem to the tips of the branches, excluding the inflorescence*).—19.7 cm.

*Width* (*plant diameter*).—31.7 cm.

*Time to produce a flowering plant.*—Plants had an average of 0.6 opened inflorescences about 9 weeks after planting rooted cuttings in Hillscheid, Germany.

*Outdoor plant performance.*—Plants continuously flower; a count in late summer of 2005 in Hillscheid, Germany produced about 20 inflorescences per plant (plants were 30-weeks-old).

Leaves:

*Arrangement.*—Alternate.

*Immature leaf color.*—Medium green. Upper surface: RHS 137C. Lower surface: RHS 138A.

*Mature leaf color.*—Upper surface: RHS 137C (medium-green). Lower surface: RHS 138A.

*Zonation color.*—RHS N200A (brown) with a medium distinctness.

*Zonation diameter.*—Inner diameter of ring: 3.2 cm. Band or belt of zonation: 1.5 cm to 2.0 cm.

*Size.*—Length: 4.3 cm. Width: 7.5 cm.

*Shape.*—Semi-circular or flabellate with distinct lobes.

*Apex.*—Lobate.

*Base.*—Truncate or obtuse.

*Margin.*—Dentate.

*Texture.*—Upper surface is smooth, dull, and velvety and the lower surface is smooth (apart from the protruding veins) and covered with fine pubescence.

*Petioles.*—Color: RHS 138A to RHS 144A (dull-green). Length: 5.0 cm to 7.0 cm. Diameter: 0.25 cm. Texture: Covered with dense pubescence.

Stems:

*Stem color.*—RHS 143C (light-green).

*Length.*—15 cm to 18 cm.

*Diameter.*—0.5 to 0.7 cm.

*Internode length.*—3.0 cm to 4.5 cm.

*Texture.*—Appears smooth but with slight pubescence.

Inflorescence bud: (just before petals unfold).

*Shape.*—Nearly round.

*Size.*—Length: 1.0 cm to 1.1 cm. Width: 0.8 cm to 0.9 cm.

*Color of sepals.*—RHS 143B (light-green).

*Color of petals.*—RHS 42A (red).

Inflorescence:

*Inflorescence type.*—An umbel composed of 25 to 40 flowers and buds.

*Umbel.*—Shape: Semi-spherical. Diameter: 7.9 cm. Height (depth): 4.5 cm.

*Lastingness of umbel on the plant.*—About 16 days.

*Peduncle.*—Color: RHS 143C (light-green). Length: 24.8 cm. Diameter: 0.3 cm to 0.4 cm. Texture: Pubescent.

*Pedicel.*—Color: RHS 143C (light-green) near the base and RHS 180A (reddish-brown) at the upper end. Length: 2.9 cm. Diameter: 0.15 cm. Texture: Short pubescence and glandular hair.

Corolla:

*Shape of corolla.*—Star-shaped, somewhat irregular with many petals, upper petals are typically distinctly longer and narrower than the other petals.

*Form.*—Double.

*Diameter.*—3.6 cm.

*Depth.*—1.2 cm.

*Number of petals.*—15 to 18.

*Petaloids.*—Number: 0 to 2. Shape: Narrow. Color: RHS 43A.

*Lastingness of individual flowers on plant.*—8 days at 18° C.

*Fragrance.*—None.

Petals:

*Shape.*—Ensiform to lanceolate or elliptical.

*Apex.*—Acute, upper petals are occasionally divided.

*Base.*—Acute.

*Margin.*—Mostly entire, weak lobes or single notches may occur.

*Texture.*—Upper surface is smooth and slightly glossy and the lower surface is glabrous.

*Upper petals.*—Length: 1.8 cm to 2.1 cm. Width: 0.3 cm to 0.4 cm. Color: Upper surface: RHS 43A (red with an orange hue). Lower surface: RHS 43B (orange-red). Markings: Some petals may develop widely apart so that the base of the petals is visible and RHS N155C (white), while some petals may develop a whitish middle line which is RHS 49D or RHS 56D for the upper surface and RHS 49D or RHS 36D for the lower surface.

*Lower petals.*—Length: 1.6 cm to 1.9 cm. Width: 0.6 cm. Color: Upper surface: RHS 43A. Lower surface: From RHS 43B to RHS 43C. Markings: Absent.

Sepals:

*Number.*—5 to 6.

*Color.*—RHS 143B (light-green) for both surfaces.

*Length.*—0.5 cm to 0.7 cm.

*Width.*—Largest upper sepal: 0.2 cm. Other sepals: 0.1 cm to 0.2 cm.

*Shape.*—Ligulate.

*Apex.*—Acute.

*Base.*—Fused.

*Margin.*—Entire.

*Texture.*—Dense glandular hair for the lower surface and the upper surface is glabrous.

Reproductive organs:

*Androecium.*—Number of anthers: 2 to 5. Filament length: 0.5 cm to 0.6 cm. Filament color: RHS 155D (white) to RHS 43B at the upper end. Pollen color: RHS 28A (orange). Pollen amount: Moderate.

*Gynoecium.*—Pistil: Number: 1. Length: 0.6 cm to 0.7 cm. Stigma color: RHS 43B (orange-red). Stigma shape: 5 to 6 lobed, at right angles, later reflexed. Style color: RHS 43B (orange-red) and fading towards the base. Style length: 0.2 cm to 0.3 cm. Style shape: Filiform (filament-like) with the lobes of the stigma initially slanting upright and later at right angles.

Fruit and seed set: No seed set observed.

Disease and insect resistance: No particular resistance or susceptibility has been observed.

COMPARISON WITH PARENTAL AND COMMERCIAL CULTIVARS

'Gradored' differs from the female parent 'K99-4006-2' (unpatented) by having red, double flowers, while 'K99-4006-2' has light-salmon, single-type flowers.

'Gradored' differs from the male parent 'K00-5693-7' (unpatented) by having red flowers with rounded inflorescences, while 'K00-5693-7' has rose-red flowers and inflorescences that are not rounded.

'Gradored' differs from the commercial variety 'Grafire' (U.S. Plant Pat. No. 16,553) by having double flowers, while 'Grafire' has single-type flowers. In addition, 'Gradored' has narrower upper petals and smaller, rounder umbels, while 'Grafire' has flatter, rather umbrella-shaped umbels.

I claim:

1. A new and distinct cultivar of *pelargonium* plant as shown and described herein.

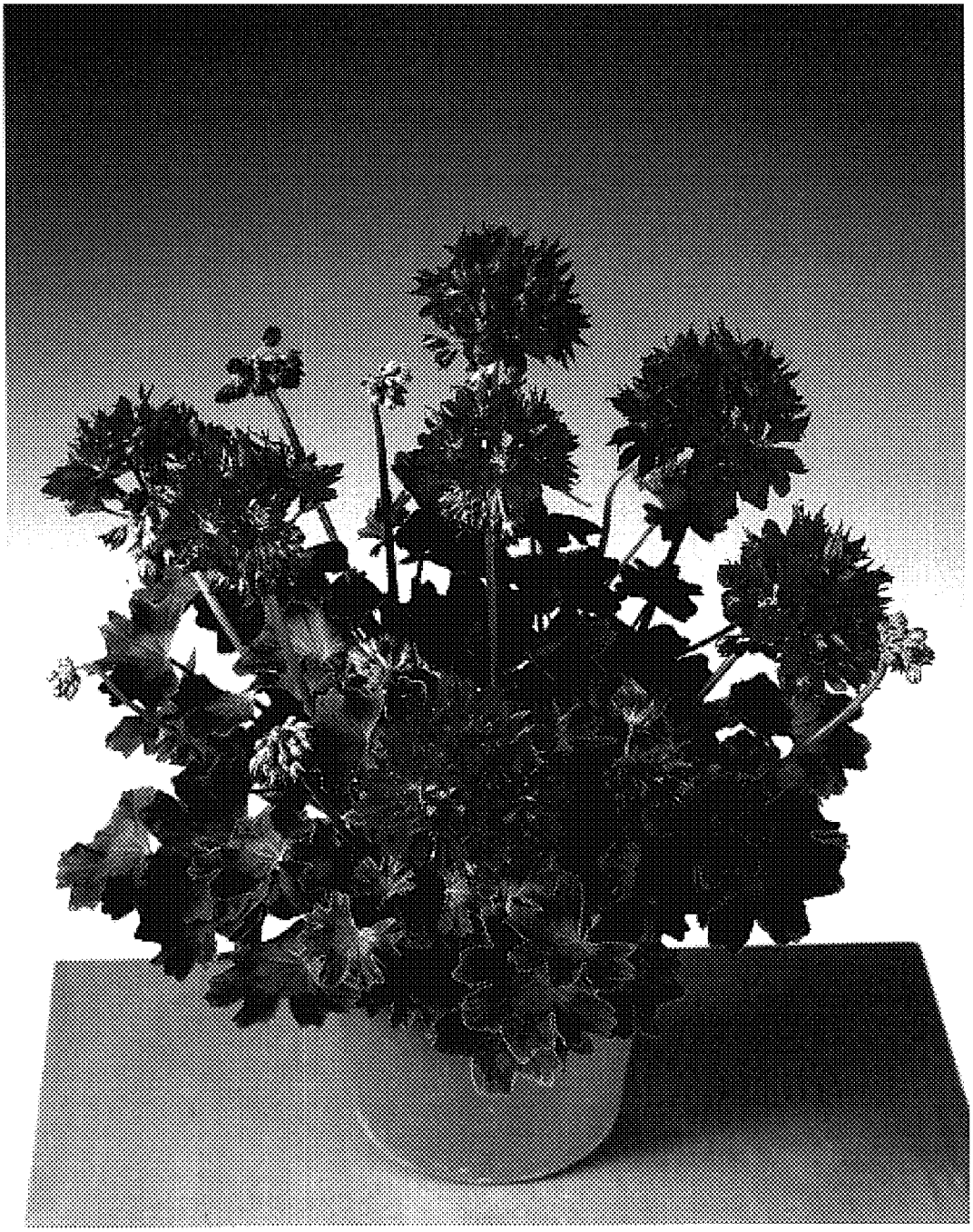

* * * * *